(12) United States Patent
Hasebe (10) Patent No.: US 9,131,976 B2
(45) Date of Patent: *Sep. 15, 2015

(54) HEATING TYPE BALLOON CATHETER DEVICE, AND ELASTIC TUBE DEVICE AND VIBRATOR DEVICE FOR THE CATHETER DEVICE

(71) Applicant: Kazunari Hasebe, Matsudo (JP)

(72) Inventor: Kazunari Hasebe, Matsudo (JP)

(73) Assignee: Toray Industries, Inc., Tokyo (JP)

(*) Notice: Subject to any disclaimer, the term of this patent is extended or adjusted under 35 U.S.C. 154(b) by 121 days.

This patent is subject to a terminal disclaimer.

(21) Appl. No.: 13/869,621

(22) Filed: Apr. 24, 2013

(65) Prior Publication Data

US 2013/0338657 A1    Dec. 19, 2013

Related U.S. Application Data

(62) Division of application No. 10/584,399, filed as application No. PCT/JP2004/000816 on Jan. 29, 2004, now Pat. No. 8,475,443.

(30) Foreign Application Priority Data

Dec. 26, 2003 (JP) ................................. 2003-432986

(51) Int. Cl.
*A61B 18/04* (2006.01)
*F04B 43/00* (2006.01)
(Continued)

(52) U.S. Cl.
CPC ....... *A61B 18/04* (2013.01); *A61B 2018/00011* (2013.01); *A61B 2018/0022* (2013.01);
(Continued)

(58) Field of Classification Search
CPC ........... A61B 2018/00005; A61B 2018/00011; A61B 2018/00202; A61B 2018/0022; A61B 2018/0046; A61B 2018/046; A61B 2018/00029; A61B 2018/00184; A61B 2018/0019; A61B 2018/00023; A61B 2018/00022; A61B 18/04; F04B 43/1253; F04B 43/0072

USPC ..................... 604/113, 131, 920; 606/27–28; 607/104–105; 417/474; 418/13, 195, 418/211

See application file for complete search history.

(56) References Cited

U.S. PATENT DOCUMENTS

| 4,160,455 A | 7/1979 | Law |
| 5,195,965 A | 3/1993 | Shantha |

(Continued)

FOREIGN PATENT DOCUMENTS

| EP | 0 801 938 | 10/1997 |
| JP | 5-293183 | 11/1993 |

(Continued)

OTHER PUBLICATIONS

International Search Report and Written Opinion mailed May 11, 2004, directed to International Patent Application No. PCT/JP2004/000816; 7 pages.

(Continued)

*Primary Examiner* — Jaymi Della
(74) *Attorney, Agent, or Firm* — Morrison & Foerster LLP (57) ABSTRACT

A heating-type balloon catheter device is provided. The catheter device may include a heating-type balloon at a top end portion of a catheter main body and a vibration imparting device connected to a base end portion of the catheter main body. The vibration imparting device may impart vibration to a liquid for heating in the heating-type balloon and include an elastic tube with a base end portion connected to the catheter main body and with a top end portion thereof closed. The elastic tube may be filled with a liquid for heating. A vibrator device having a roller rotating about a rotary shaft at a position offset to the rotary shaft may be provided. A margin volume part which is not pressed with the roller is provided on the side of the top end portion of the elastic tube.

4 Claims, 4 Drawing Sheets (51) Int. Cl.
 *F04B 43/12* (2006.01)
 *A61B 18/00* (2006.01)

(52) U.S. Cl.
 CPC . *A61B2018/00023* (2013.01); *A61B 2018/046* (2013.01); *F04B 43/0072* (2013.01); *F04B 43/1253* (2013.01)

(56) References Cited

U.S. PATENT DOCUMENTS

| | | | |
|---|---|---|---|
| 5,215,450 | A | 6/1993 | Tamari |
| 5,549,559 | A | 8/1996 | Eshel |
| 5,735,817 | A | 4/1998 | Shantha |
| 6,146,411 | A | 11/2000 | Noda et al. |
| 6,223,085 | B1 | 4/2001 | Dann et al. |
| 2001/0056257 | A1 | 12/2001 | Drasler et al. |
| 2003/0065371 | A1 | 4/2003 | Satake |
| 2007/0243088 | A1* | 10/2007 | North ........................ 417/477.1 |

FOREIGN PATENT DOCUMENTS

| | | |
|---|---|---|
| JP | 6-327763 | 11/1994 |
| JP | 10-33582 | 2/1998 |
| JP | 2003-102850 | 4/2003 |
| JP | 2003-111848 | 4/2003 |
| WO | WO-96/15741 | 5/1996 |
| WO | WO-03/030789 | 4/2003 |

OTHER PUBLICATIONS

Hasebe, K., Office Action mailed Nov. 9, 2010, directed to U.S. Appl. No. 10/584,399; 15 pages.

Hasebe, K., Office Action mailed Apr. 28, 2011, directed to U.S. Appl. No. 10/584,399; 14 pages.

Hasebe, K., Office Action mailed Oct. 2, 2012, directed to U.S. Appl. No. 10/584,399; 11 pages.

* cited by examiner

HEATING TYPE BALLOON CATHETER DEVICE, AND ELASTIC TUBE DEVICE AND VIBRATOR DEVICE FOR THE CATHETER DEVICE

REFERENCE TO RELATED APPLICATIONS

This application is a divisional of U.S. patent application Ser. No. 10/584,399, filed Jun. 4, 2007, which is a national stage application under 35 USC 371 of International Application No. PCT/JP2004/000816, filed Jan. 29, 2004, which claims priority from Japanese patent application No. 2003-432986, filed Dec. 26, 2003, the disclosures of which are incorporated herein by reference.

FIELD OF THE INVENTION

The present invention relates to a heating-type balloon catheter device designed to make the temperature of heating liquid in a balloon uniform by utilizing vibration of the heating liquid, as well as an elastic tube device and a vibrator device for use with the catheter device.

BACKGROUND OF THE INVENTION

A balloon catheter which is fitted with a balloon at a distal top end portion of the main body of the catheter is provided therein with a heating means. The heating liquid filled in the balloon is heated with the heating means, and the heated balloon is brought into contact with the body tissues, thereby locally cauterizing and consequently treating the body tissues. The balloon is further provided with a thermocouple acting as a thermosensor for detecting the temperature of the heating liquid.

The heating-type balloon catheter device is desired in some cases to be used for cauterizing a considerably wide area of the body tissues with the balloon. To be more specific, for instance, if an abnormal path (an accessory conduction passage) would exist over a passage of electrical signals for moving the heart, it may cause symptoms such as vertigo and sick sensation which are referred to as atrial fibrillation. The atrial fibrillation may further cause the deterioration of cardiac incompetence or constitute a serious cause for brain infarction. In order to cut off the abnormal conduction path formed in the pulmonary vein, an edge portion of the opening of the pulmonary vein opening toward the left ventricle (the pulmonary vein orifice) is desirably cauterized totally, i.e., in an annular fashion.

As described above, in the event where the heating liquid filled in the balloon is heated while sustaining the temperature to be detected with the thermocouple fitted in the balloon to a predetermined temperature in a state in which the balloon is in annular contact with the pulmonary vein as a whole, it has been found that an event may be caused to occur where a state in which the pulmonary vein is cauterized in a peripheral direction may vary to a considerable extent. In other words, it has been found that this event may lead to a state in which a certain portion of the pulmonary vein orifice is over-heated while the other portion thereof is heated to a lesser and insufficient level.

Japanese Patent Application Publication No. 2003-111, 848 discloses the technique in which heating liquid filled in the balloon is stirred by utilizing vibration in order to uniform the temperature of the heating liquid in the balloon. More specifically, the device of this type is constructed in such a manner that a vibration imparting device for imparting vibration is connected to the base end portion of a catheter main body and a passage extending from the vibration imparting device to the balloon is filled with the heating liquid so as to transmit the vibration imparted with the vibration imparting device to the heating liquid in the balloon through the heating liquid within the catheter main body.

Some devices for imparting vibration are proposed, which include a device of the type that utilizes a diaphragm drivable reciprocally with a motor or a device of the type that expands or contracts an elastic tube connected to the base end portion of the catheter main body in its radial direction with a member drivable reciprocally.

It is to be noted herein that the balloon having a different size may be used selectively by complying with a variation in the body size of a patient or a site of cauterization or the like. The size of the balloon may be 20φ, 25φ, or 30φ for example.

As described above, it has been found that, in the event that the size of the balloon is varied, an undesirable deformation in expansion and shrinkage of the balloon would be caused to occur due to a difference in uniformity of the temperature of the heating liquid in the balloon even if an equivalent or similar level of vibration would be imparted to the vibration imparting device. In other words, in the event that an appropriate level of vibration is set to a smaller-sized balloon, the extent of vibration (e.g., the extent of stirring) may be too small for a larger-sized balloon, thereby resulting in the likelihood that the temperature of the heating liquid within the balloon remains irregular. Conversely, in the event that an appropriate level of vibration is set to a larger-sized balloon, it is too large for a smaller-sized balloon, thereby causing a repetition of expansion and shrinkage of the balloon to a great extent. In other words, problems may likely occur that the balloon is caused to come into contact with the site of cauterization (if the balloon would expands too much), while the balloon is positioned apart from the site of cauterization (if the balloon would shrink too much).

SUMMARY OF THE INVENTION

A heating-type balloon catheter device is provided. The catheter device may include a heating-type balloon at a top end portion of a catheter main body and a vibration imparting device connected to a base end portion of the catheter main body. The vibration imparting device may impart vibration to a liquid for heating in the heating-type balloon and include an elastic tube with a base end portion connected to the catheter main body and with a top end portion thereof closed. The elastic tube may be filled with a liquid for heating. A vibrator device having a roller rotating about a rotary shaft at a position offset to the rotary shaft may be provided. The elastic tube may be set to such a vibrator device so that a predetermined direction of rotation of the roller extends from the side of the base end portion of the elastic tube to the side of the top end portion thereof and a margin volume part which is not pressed with the roller is provided on the side of the top end portion of the elastic tube.

DETAILED DESCRIPTION OF THE INVENTION

The present invention has the first object to provide a heating-type balloon catheter device that can provide a balloon with vibration having the magnitude appropriate for the size of the balloon and that can thoroughly block a vibration site to which to impart vibration and a contact site to be brought into contact with a heating liquid.

The second object of the present invention is to provide an elastic tube device for use with the heating-type balloon catheter device of the present invention.

The third object of the present invention is to provide a vibrator device for imparting an appropriate level of vibration upon use with the heating-type balloon catheter device of the present invention.

In order to achieve the first object as described above, the present invention adopts the solution as will be described hereinafter. The solution resides in that a heating-type balloon catheter device is provided which comprises:

a catheter main body fitted at its top end portion with a heating-type balloon; and a vibration-imparting device connected to a base end portion of the catheter main body, the vibrator device being provided for imparting vibration to a heating liquid filled in the heating-type balloon through a heating liquid filled in the catheter main body;

wherein the vibration-imparting device comprises an elastic tube in which the heating liquid is to be filled, the elastic tube being connected at its base end portion to the catheter main body and closed at its top end portion; and a vibrator device having a roller rotatable around a rotary shaft at a position offset with respect to the rotary shaft and being provided with the elastic tube;

wherein the elastic tube is provided with the vibrator device in such a way that a predetermined direction of rotation of the rotary shaft is set to be directed from the side of the base end portion of the elastic tube toward the side of the top end portion thereof and that a margin volume part is ensured on the side of the top end portion of the elastic tube, which is constructed so as not to be pressed with the roller;

wherein the elastic tube is structured to assume a shut-off state and a communication state in accordance with rotation of the roller in the predetermined direction of rotation thereof in such a way that the shut-off state is set to a state in which the base end portion of the elastic tube and the top end portion thereof are blocked by constriction or decrease of a radial size of the elastic tube by pressing the elastic tube with the roller in the predetermined direction of rotation, and the communication state is set to a state in which the base end portion thereof is communicated with the top end portion thereof by expansion or increase of the reduced radial size of the elastic tube due to elasticity of the elastic tube by releasing the pressing of the roller upon the elastic tube; and wherein, in accordance with the rotation of the roller in the predetermined direction of rotation thereof, pressure is applied to the heating liquid in the elastic tube toward the margin volume part, one the one hand, during a period when the elastic tube is in the shut-off state, and the heating liquid to which pressure is applied in the margin volume part is flown backward toward the base end portion of the elastic tube, on the other hand, during a period when the elastic tube is in the communication state.

In accordance with the above solution, the heating liquid is provided with pressure toward the margin volume part, on the one hand, by pressing the elastic tube with the roller, that is, by constricting or decreasing the radial size of the elastic tube, and the pressured heating liquid within the margin volume part is allowed to flow backward toward the catheter main body side, i.e., the balloon side, on the other hand, by separating the roller apart from the elastic tube, that is, expanding or increasing the radial size of the elastic tube. The application of pressure and the backward flow of the heating liquid may be performed at repeated times in accordance with the rotation of the rotary shaft. In the event where a larger-sized balloon is to be applied, the way of setting the elastic tube to the roller-type vibrator device is changed simply in such a manner that the margin volume part becomes larger than the balloon being smaller in size. In other words, in the event that the balloon is a larger one, the elastic tube can be set to the roller-type vibrator device in such a manner that the margin volume part becomes larger in volume while the balloon is smaller in size. This setting permits an appropriate level of vibration energy to be obtained in accordance with the size of the balloon. It is further noted as a matter of course that the cycle of vibration can be readily varied with the number of rotation of the rotary shaft.

Moreover, as the roller-type vibrator device is separated thoroughly from the heating liquid through the elastic tube, the heating-type balloon catheter device according to the present invention is advantageous from the point of view of cleanliness.

In addition, as the vibrator device of the present invention is of the type utilizing the rotary movement alone, the vibrator device can be made simpler in structure than the conventional one that utilizes the reciprocal movement. Furthermore, the vibrator device according to the present invention can be structured by using a conventional roller pump in an efficient way.

The preferred embodiments on the premise of the above-mentioned solutions are as described in claims 2 to 10. More specifically, the elastic tube is connected to a base end portion of the catheter main body through an extension tube which is superior in rigidity and unlikely to be deformed by expanding or constricting in a radial direction thereof (as described in claim 2). In this embodiment, the vibrator device can be fitted at a position apart from the catheter main body. It is to be noted herein as a matter of course that, as the extension tube is made of a material unlikely to be deformed by expanding or constricting, the vibration is not caused to be damped at the extension tube portion to a great extent.

To the base end portion of the catheter main body is a connecter having a plurality of branch passages. The elastic tube can be connected to a predetermined branch passage for supplying a contrast agent, among the branch passages (as described in claim 3). In this embodiment, the vibration can be transmitted to the balloon by effectively utilizing the branch passage for supplying the contrast agent.

The elastic tube is connected to the predetermined branch passage through a shift valve that can assume a first shift position and a second shift position, the first shift position being structured to block the communication of the elastic tube with the catheter main body in order to supply the catheter main body with the contrast agent and the second shift position being structured to communicate the elastic tube with the catheter main body (as described in claim 4). In this embodiment, the shift valve can easily shift the position from a state of supplying the contrast agent to a state of imparting vibration and vice versa.

The elastic tube can be provided at an outer peripheral surface thereof with an indicator indicating the size of the margin volume part to be set in accordance with the size of the balloon (as described in claim 5). In this embodiment, the indicator allows an easy and optimum setting of the size of the margin volume part in accordance with the size of the balloon.

The indicator can be set by setting a predetermined position of a housing with respect to the vibrator device as a reference (as described in claim 6). This embodiment permits an optimum setting of the size of the margin volume part in accordance with the size of the balloon solely simply by aligning the indicator with the predetermined position of the housing with respect to the vibrator device to which the elastic tube is to be connected.

It is preferred that the predetermined position of the housing is set at the edge surface of an orifice on the inlet side or in its vicinity thereof and at a position that can be readily visible from the outside. The indicator can be set in a plural number at spaced intervals disposed in the direction toward the base end portion side of the elastic tube from the top end side thereof (as described in claim 7). In this embodiment, the size of the margin volume part can be set in an extremely easy and accurate way in accordance with the size of the balloon simply by confirming the position visibly.

In a predetermined path extending from the base end portion of the catheter main body to the top end of the elastic tube, at least one air vent valve for venting air within the predetermined path is provided (as described in claim 8). This is a preferred embodiment in order to vent the air present in the area extending from the balloon to the top end of the elastic tube to a thorough or adequate extent by venting the air from the area most remote from the balloon, thereby enabling a surer transmission of the vibration to the balloon.

The air vent valve can be connected to the top end of the elastic tube (as described in claim 9). The connection of the air vent valve is preferred in order to vent the air present in the area extending from the balloon to the top end of the elastic tube to a complete or adequate extent by venting the air from the position most remote from the balloon.

The air vent valve may comprise a first air vent valve and a second air vent valve, the first air vent valve being connected to a path extending from the catheter main body to the elastic tube and the second air vent valve being connected to the top end of the elastic tube (as described in claim 10). This embodiment is preferred in order to thoroughly or adequately vent the air present within the path to be filled with the heating liquid even in such a state that the elastic tube is pressed with the roller.

In order to achieve the above second object, the present invention adopts the solutions as will be described below, i.e., in claim 11. The subject matter of claim 11 is directed to the elastic tube that is structured in such a manner that the tube wall portions of the elastic tube on the opposite sides can be closely attached to each other in the radial direction, on the one hand, as external force is applied in the radial direction from the outside to constrict or reduce the radial size of the elastic tube and that they can, be recovered elastically to their original positions, on the other hand, as the external force is released. The elastic tube can be closed at its top end comprise a connection portion at which the base end portion of the tube is connected to the catheter main body. The elastic tube may be provided at its outer peripheral surface with plural indicators at spaced intervals in the longitudinal direction thereof, the indicator corresponding to the size of the balloon in the heating-type balloon catheter device. In accordance with the above solutions, an elastic tube device can be provided, which can be used for the heating-type balloon catheter device as described in claim 1 and have the indicator for setting the size of the margin volume part is disposed.

Preferred embodiments on the premise of the above solutions are described in each of claims 12 to 14, which can provide the elastic tube device having the plural indicators disposed at spaced intervals in the area extending from the top end portion side of the elastic tube toward the base end portion thereof (as described in claim 12). This preferred embodiment can provide the elastic tube device as being preferably applied to the heating-type balloon catheter device as described in claim 7.

In another preferred embodiment, the air vent valve can be disposed at either one of the top end or the base end of the elastic tube in order to selectively vent the air within the elastic tube to the atmosphere (as described in claim 13). This embodiment can provide the elastic tube device having the function of venting the air from the path extending from the balloon to the elastic tube.

In a further preferred embodiment, the elastic tube can be provided with the air vent valves at each of the edge and the base end portions thereof in order to enable a selective ventilation of the air present in the elastic tube (as described in claim 14). This preferred embodiment can provide the elastic tube device capable of venting the air from the path extending from the balloon to the top end of the elastic tube.

In order to achieve the third object, the present invention adopts the solutions as will be described below, i.e., as described in claim 15, which comprise:

a housing;

a rotary shaft held pivotally to the housing;

a guide surface formed on the inner peripheral surface of the housing in such a way to enclose the rotary shaft and formed in an arc shape disposed around the rotary shaft; and a roller for pressing the elastic tube in cooperation with the guide surface disposed in such a way to rotate about the rotary shaft at a position offset from the rotary shaft;

wherein the number and/or the arrangement of the roller are/is set to assume a state in which the roller is not disposed at the position opposite to or facing the guide surface and the roller cannot press the elastic tube as the rotary shaft is rotated at one full revolution. The above solution can provide the vibrator device which can be used appropriately for the heating-type balloon catheter device as described in claims 1 to 10.

Other preferred embodiments on the premise of the above solutions are described in claims 16 et seq. More specifically, the preferred embodiment comprises one roller and the guide surface set at an angle in the range of approximately 180 degree round the rotary shaft as the center (as described in claim 16). This preferred embodiment can minimize the number of the rollers to only one. This preferred embodiment can also set the time for applying pressure to the margin volume part and the time for flowing backward the heating liquid from the margin volume part to be approximately equal.

Another preferred embodiment can comprise two rollers disposed each at an interval of 180 degree round, the rotary shaft and the guide surface set each at an angle in the range of approximately 60 degree round the rotary shaft (as described in claim 17). In this embodiment, the application of pressure and the backward flowing can be conducted each two times per one full revolution of the rotary shaft. This preferred embodiment can set the time for applying pressure for the first time and the time for flowing backward for the first time as well as the time for applying pressure for the second time and the time for flowing backward for the second time per one full revolution to be substantially equal to each other.

In another preferred embodiment, the roller system can comprise two rollers consisting of a front roller and a rear roller, the front roller being disposed on an advance side in a predetermined direction round the rotary shaft and the rear roller being disposed on a delay side in the predetermined direction. The front and rear rollers may be disposed in the proximity to each other in the direction of rotation of the rotary shaft and arranged to assume a position at which they are opposite to or face the guide surface and a position at which they are not opposite to or face the guide surface as the rotary shaft rotates one full revolution. Further, as each of the front and rear rollers are arranged at the positions opposite to the guide surface, the distance spaced between the front roller and the guide surface is set to become somewhat larger than the distance spaced between the rear roller and the guide surface (as described in claim 18). This embodiment is preferred in order to impose no crashing external force (pressure) onto the elastic tube, as compared with the case where the elastic tube is pressed down once with one roller, because in this preferred embodiment the elastic tube can be contracted to a considerable extent with the front roller in advance before it is thoroughly closed with the rear roller.

In accordance with the present invention, the magnitude of vibration energy to be applied to the heating liquid can be appropriately set in order to comply with the size of the balloon. Further, the vibrator device as a source of vibration can be blocked thoroughly from the heating liquid through the elastic tube so that the device is preferred in terms of cleanliness. Moreover, the vibrator device allows an effective use of a conventional roller pump so that the device can be made simple in structure because it utilizes the rotary motion alone.

In addition, the present invention can provide the elastic tube device for use with the heating-type balloon catheter device of the present invention and the vibrator device appropriate for use with the heating-type balloon catheter device of the present invention.

Exemplary Embodiments

Figure 1:
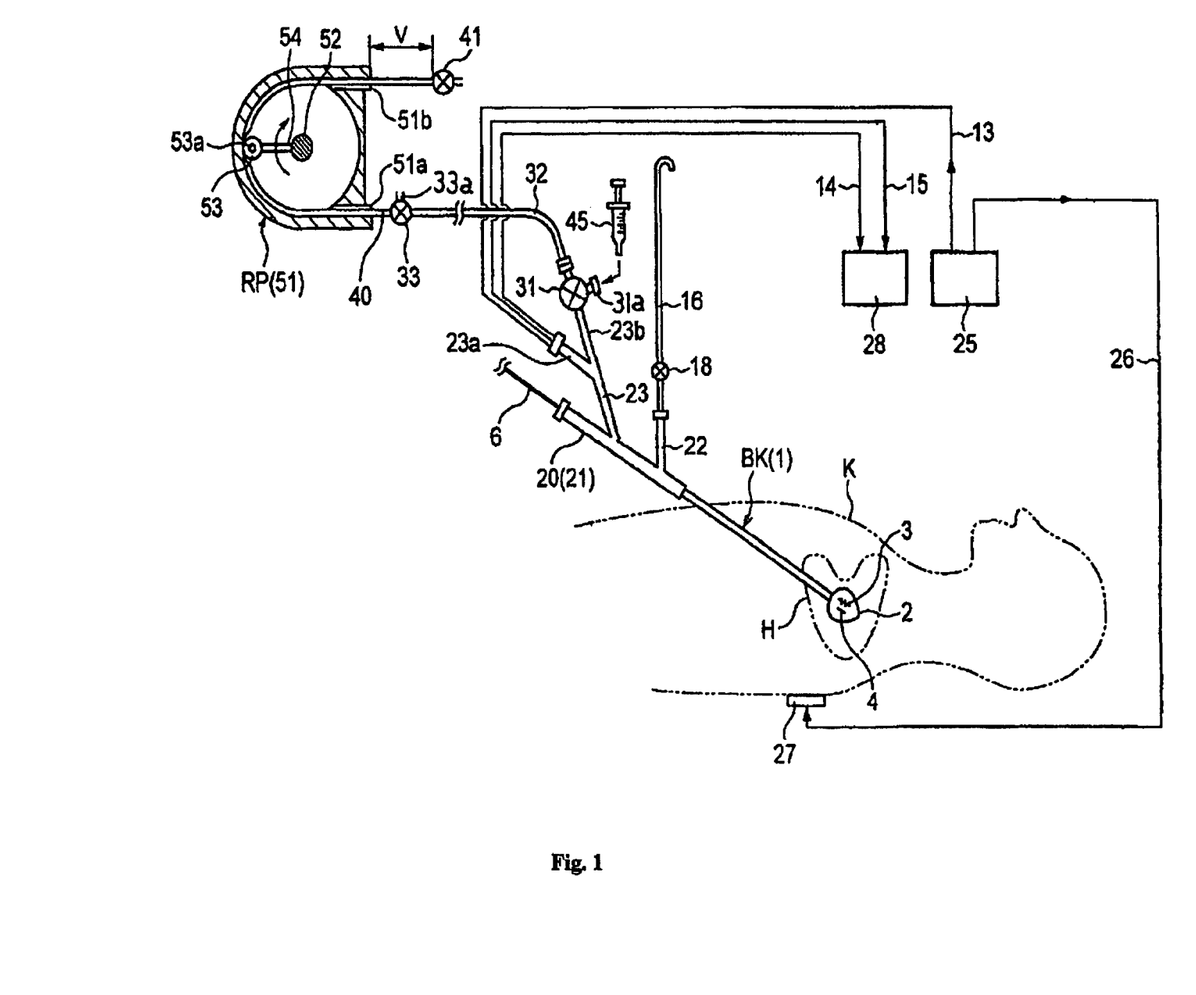
FIG. 1 is a system diagram showing an example of the present invention.

As shown in FIG. 1, a catheter BK is inserted percutaneously into a predetermined site of the heart H of a patient K from the outside of the body. The catheter BK is of a heating-type balloon catheter type and a catheter main body 1 in the form of a tube is provided at its top end portion with a balloon 2. The balloon 2 is fitted with a high-frequency heating electrode 3 as a heating means and a thermocouple 4 as a temperature sensor, as will be described hereinafter in more detail.

Figure 2:
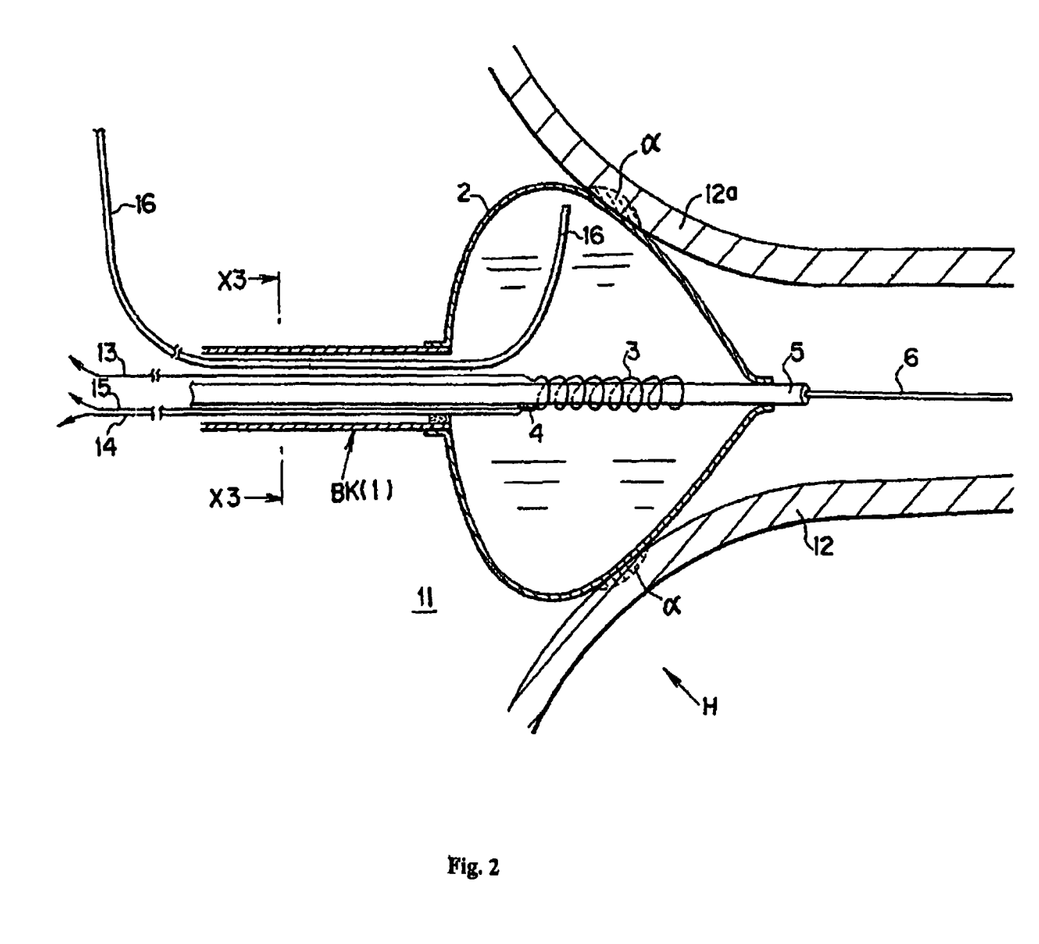
FIG. 2 is a side view in section showing an essential portion of the case where the orifice of the pulmonary vein is cauterized.

As shown in FIG. 2, the catheter main body 1 is fitted therewith a guide tube 5 having a size substantially smaller than the size of the catheter main body 1. The guide tube 5 has a length approximately equal to the length of the catheter main body 1 and the top end portion of the guide tube 5 is formed in a form projecting somewhat from the top end portion of the catheter main body 1. A guide wire 6 is further fitted to move through the inside of the guide tube 5.

The balloon 2 is disposed in such a manner as bridging between the top end portion of the catheter main body 1 and the top end portion of the guide tube 5. In the balloon 2, the heating electrode 3 is disposed in such a manner as winding the guide tube 5, and the thermocouple 4 is further fixed to the guide tube 5.

FIG. 2 shows the case where the accessory transmission passage from the pulmonary vein 12, which becomes a cause of atrial fibrillation, is cauterized with the heating-type balloon catheter device. More specifically, it is shown therein that the top end portion of the catheter main body 1, i.e., the balloon 2, is disposed at the position corresponding to the left ventricle 11, and the expanded balloon 2 is in annular contact with the pulmonary vein orifice 12a which is an orifice edge portion to the left ventricle 11 of the pulmonary vein 12. In FIG. 2, the site of cauterization is an annular site at which the balloon 2 is brought in contact with the pulmonary vein orifice 12a and this site is represented by reference symbol α.

Figure 3:
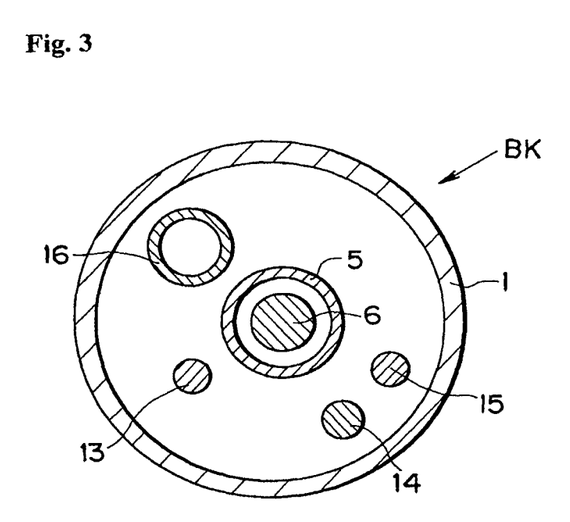
FIG. 3 is a view in section taken along the line 3-3 of FIG. 2.

The wire 13 extending from the heating electrode 3 as well as a pair of wires 14 and 15 extending from the thermocouple 4 are disposed to extend through the catheter main body 1 and reach eventually into the body as will be described hereinafter. The catheter main body 1 is further provided therein with an air vent tube 16 for venting the air present in the balloon 2. The air vent tube 16 is provided in such a manner that the top end portion thereof has an aperture opening to the inside of the balloon 2 at its higher position and the other edge portion thereof is open toward the atmosphere at a higher position of the outside of the body. Elements 5, 6 and 13-16 are disposed in the catheter main body 1 as are illustrated schematically in FIG. 3.

As shown again in FIG. 1, the base end portion of the catheter main body 1, i.e., the portion disposed outside the body, is connected to a connecter 20. The connecter 20 comprises a main passage 21, a first branch passage 22 and a second branch passage 23, the main passage 21 extending on a plane approximately with the catheter main body 1 in the axial direction as well as the first branch passage and the second branch passage each being branched from the main passage 21. The second branch passage 23 is further branched into two branch passages 23a and 23b.

The guide wire 6 is disposed to pass through the main passage 21 of the connecter 20 and extend outside the body. A hemostatic valve for preventing a backward flow of the blood is disposed at the site at which the guide wire 6 is led to the outside of the body from the main passage 22.

The air vent tube 16 is drawn from the first branch passage 22 and extends toward a higher position (while the site of drawing the tube is sealed). To the air vent tube 16 is connected a switch valve 18 which is disposed to be closed after supplying the balloon 2 with the heating liquid, i.e., at the time when vibration is imparted to the balloon 2, as will be described in more detail hereinafter.

The wires 13, 14 and 15 are led from the branch passage 23a to the outside of the body, and the site of leading outside the body is sealed. The wire 13 for the heating electrode 3 is connected to a high frequency (high-frequency voltage) generating device 25 from which a wire 26 paired with the wire 13 extends and is connected to an outside electrode 27 which is brought into contact with the body surface. By operating the high-frequency generating device 25 in a state in which the electrode 3 is disposed at the predetermined site in the body as shown in FIG. 2 and the outside electrode 27 is in contact with the body surface, high frequency is turned on between the two electrodes 3 and 27 to heat the heating electrode 3.

The wires 14 and 15 each extending from the thermocouple 4 are connected each to a temperature measurement device 28 utilizing a thermometer. A difference of voltage in accordance with the temperature within the balloon 2 is input to the thermometer 28 through the two wires 14 and 15, and the temperature inside the balloon 2 can be detected and indicated.

The branch passage 23b is fitted with a shift valve 31 which in turn is connected to an elastic tube 40 through an extension tube 32. A three-way shift valve is used for the shift valve 31 that is arranged to selectively assume a first shift position and a second shift position, the first shift position being disposed to connect the branch passage 23b to the extension tube 32 and the second shift position being disposed to connect the branch passage 23b to a connection orifice 31a opening to the air (at this time, the extension tube 32 and the branch passage 23b are blocked). In other words, as the shift valve 31 assumes the second shift position, on the one hand, a contrast agent and so on is supplied to the balloon 2 via the branch passage 23b from a syringe 45 to be connected to the connection orifice 31a. As the shift valve 31 assumes the first shift position, on the other hand, the connection orifice 31a is closed.

The extension tube 32 is connected to the elastic tube 40 via the first air vent valve 33 which comprises a three-way shift valve that in turn can shift the position of the extension tube 32 selectively between a first shift position and a second shift position in accordance with the shift position. The first shift position is the position at which the extension tube 32 is connected to the elastic tube 40 in an airtight way and the second shift position is the position at which the extension tube 32 and the elastic tube 40 are connected to an orifice 33a opening to the atmosphere. The extension tube 32 comprises a pressure-proof tube which may be made of a material having high rigidity and unlikely to be deformed by expansion and constriction, yet likely to be curved in a relatively easy manner. The length of the extension tube 32 may be set to be as long as approximately 1,300 mm or the like.

The elastic tube 40 may be made of a silicone tube for example, having a length of approximately 300 mm. The elastic tube 40 is set to a vibrator device RP of a roller type. The details of the vibrator device RP will be described with reference to FIG. 4. The vibrator device RP comprises a housing 51 and a rotary shaft 52 held pivotally to the housing 51. The housing 51 is provided at its inner surface with a guide surface G in an arc-shaped form round the rotary shaft 52. The guide surface G is formed at an angle in the range of approximately 180 degree (in a generally semi-circular form) in the direction of rotation of the rotary shaft 52. The rotary shaft 52 is provided with a roller 53 through a holding rod 54. The roller 53 is fitted by the holding rod 54 in such a manner as rotating round the axis 53a. This mode enables the roller 53 to be rotated round the shaft 53a (turn on its axis) and rotated round the rotary shaft 52 (move in an orbital manner).

Figure 4:
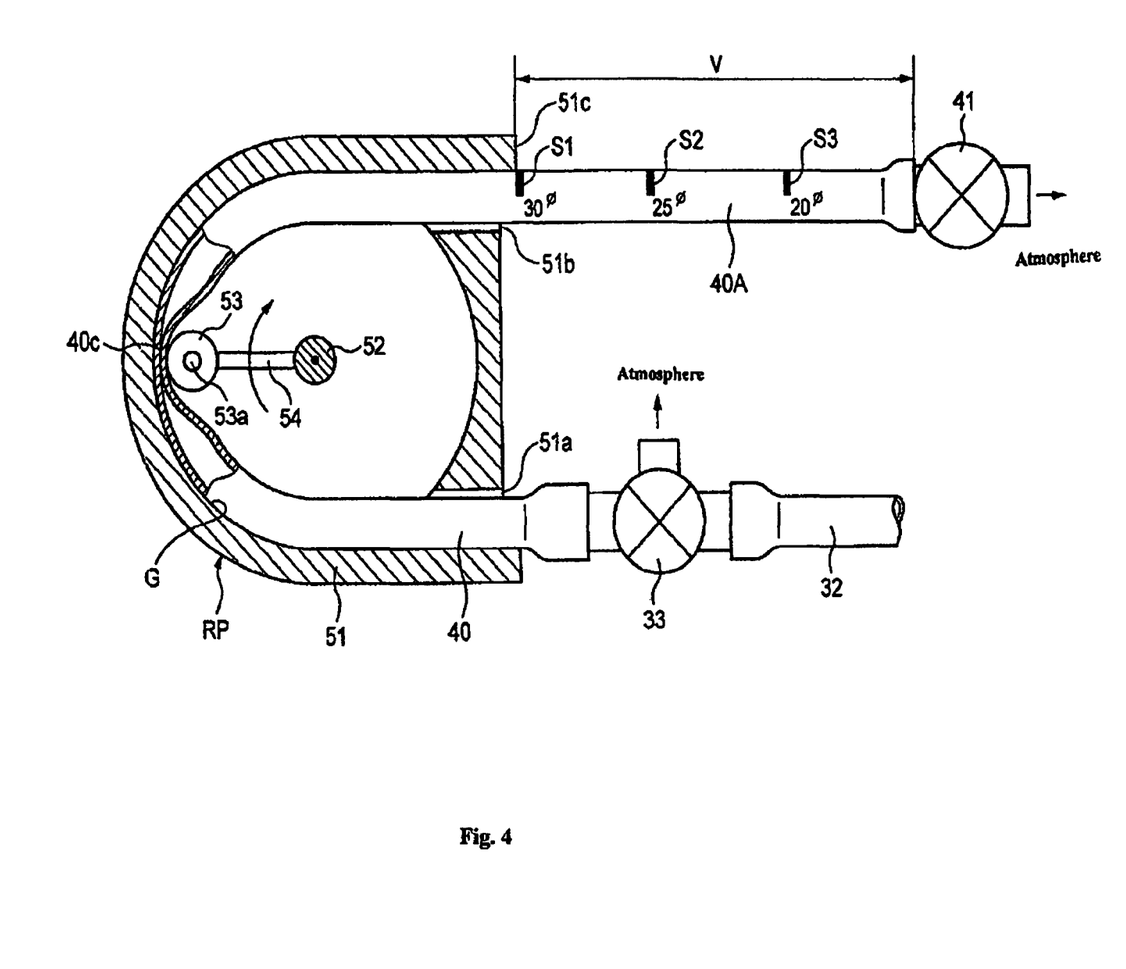
FIG. 4 is a plan view in partial section showing the detail of the vibrator device with the elastic tube set thereto.

The guide surface G is disposed at a position deviated outward from a locus of rotation of the roller 53 round the rotary shaft 52 by a predetermined distance that may be as long as twice the length of the tube wall of the elastic tube 40. In other words, in the event where the elastic tube 40 is disposed (set) along the guide surface G, the elastic tube 40 is caused to completely constrict or reduce the size of the elastic tube 40, i.e., to be closed thoroughly in the radial direction (i.e., the tube walls of the elastic tube 40 opposite to each other are closely attached to each other) at a position at which the roller 53 is located opposite to the guide surface (i.e., at an angle in the range of approximately 180 degree about the rotary shaft 52).

The housing 51 is provided with an inlet 51a and an outlet 51b. The elastic tube 40 is disposed along the guide surface G and extends from the inlet 51a and the outlet 51b to the outside of the housing 51 (i.e., the elastic tube 40 is set in such a state that it is curved in a generally U-shaped form as a whole). The length of projection of the elastic tube 40 from the inlet 51a is set to be short and the first air vent valve 33 is disposed at a position immediately close to the inlet 51a.

The portion of the elastic tube 40 projecting from the outlet 51b constitutes a margin volume part 40A and the length (size) of the margin volume part 40A is represented by reference symbol V. The length V of the margin volume part 40A is set (altered) to become a predetermined length in accordance with the size of the balloon 2 (indicated by the volume or the diameter corresponding to the volume). The top end of the elastic tube 40, i.e., the top end of the portion projecting from the outlet 51b, is fitted with the second air vent valve 41 which comprises an switch valve to selectively shift between a state in which the top end of the elastic tube 40 is closed and a state in which the elastic tube 40 is opened to the air.

The elastic tube 40 is provided with indicators S1, S2 and S3 at its outer peripheral surface on the side of the top end portion thereof. The orifice edge surface 51c of the outlet 51a of the housing 51 is set at a predetermined reference position corresponding to the indicators S1 to S2, inclusive. Among the indicators S1 to S2, the indicator S3 is disposed at a position closest to the top end of the elastic tube 40 (i.e., the second air vent valve 41), while the indicator S1 is disposed at a position most remote from the top end of the elastic tube 40. The indicator S2 is disposed at a position between the indicators S1 and S3.

By altering the indicator to be aligned with the orifice edge surface 51c, the length of the margin volume part 40A can be altered. A description will be made concerning the setting of the length of the margin volume part 40A as a specific example. In this example, the length of the catheter main body 2 is set to 800 mm (an outer diameter set to 5 mm), a 4×8 300-mm silicone tube is used as the elastic tube 40, a 1,300-mm pressure-proof tube is used as the extension tube 32 (the diameter is set to be equal to that of the elastic tube 40), and the length of the guide surface G (i.e., the length in an angle in the range of approximately 180 degree about the rotary shaft 52) is set to 160 mm. First of all, in a state of FIG. 4 in which the indicator S1 as a reference position is aligned with the orifice edge surface 51c, this state corresponds to the position appropriate for the balloon 2 having a size as large as 30ϕ for example (in this case, the reference symbol V is set to 140 mm for example, when the length of the margin volume part 40A is represented by reference symbol V). For example, when the indicator S2 is aligned with the orifice edge surface 51c, the length of the margin volume part 40 is set to be shorter than the length as expressed by the reference symbol V (V being set to 90 mm for example). The position in this case is appropriate when the balloon 2 has a size as large as 25ϕ. Moreover, when the indicator S3 is aligned with the orifice edge surface 51c, the length of the margin volume part 40A is set to be shorter (40 mm for example). The position in this case corresponds to the position appropriate for the balloon 2 having a size as large as 20ϕ for example.

The rotary shaft 52 is driven rotatively in the predetermined direction of rotation (a motor for rotatively driving being not shown in the drawing). The predetermined direction of rotation is defined as a direction in which the roller 53 is directed from the side of the inlet 51a to the side of the outlet 51b round the rotary shaft 52, that is, as a direction in which it move in an orbit motion from the base end portion of the elastic tube 40 (a connection part to the extension tube 32) to the side of the outlet 51b (the side of the second air vent valve 41).

The elastic tube 40 is thoroughly deformed by crushing or flattening the radial size of the elastic tube 40 at a position where the roller 53 is disposed opposite to the guide surface G (i.e., the opposite tube walls of the elastic tube 40 are closely attached to each other), and the side of the base end portion of the elastic tube 40 and the side of the top end portion of the elastic tube 40 are blocked on the boundary of the portion whose size is crushed or flattened. The margin volume part 40 is provided with pressure in accordance with the movement of the roller 53 in the predetermined direction of rotation. On the other hand, the side of the base end portion of the elastic tube 40 is communicated with the side of the top end portion of the elastic tube 40 at the position where the roller 53 is not opposite to the guide surface G because the flattened portion of the elastic tube 40 is recovered to its original size by the action of recovering elasticity. In other words, in the event that the flattened portion of the elastic tube 40 is expanded and returned to its original size, the pressure applied to the margin volume part 40A is released (i.e., flown backward) toward the base end portion thereof.

The heating liquid in the margin volume part 40A pressurized by applying pressure thereto at the time when the size of the elastic tube 40 is crushed or flattened in a state in which the path extending from the elastic tube 40 to the balloon 2 is filled with the heating liquid is then flown backward toward the balloon 2 as the elastic tube 40 is expanded. The vibration can be transmitted from the margin volume part 40A to the balloon 2 by repeating the crushing or flattening of the size of the elastic tube 40 and the expansion of the crushed or flattened size thereof. As a result, the heating liquid is stirred to make the temperature of the heating liquid uniform. Although a larger magnitude of vibration energy is required for making the temperature of the heating liquid uniform in the event where the balloon 2 having a larger size is used, such a large magnitude of the vibration energy can be obtained by making the length of the margin volume part 40A larger.

Although the frequency of vibration is desired in the highest possible number, the vibration cannot be effectively transmitted to the balloon 2 if the high frequency is damped on its way. Therefore, the frequency of the vibration is preferably set to approximately 2 Hz for example, as in the specific case as has been described above. In this case, the rotary shaft 52 may be rotated by two full revolutions per second. It can be noted herein as a matter of course that, as the number of rotation of the rotary shaft 52 is set higher, the frequency of the vibration is made higher.

Next, a description will be made of the action of the construction of the present invention as has been described above. First, at the initial stage, the shift valve 31 is in a state in which the branch passage 23b is communicated with the connection orifice 31a and the shift valve 31 is not connected to the extension tube 32. In this state, the guide wire 6 is inserted cutaneously into the body from the outside of the body in such a state that the top end portion thereof is inserted to some extent into the pulmonary vein 12 via the left ventricle 11. The catheter main body 1 can then be inserted into the body (by inserting the guide wire 6 through the guide tube 5) as it is guided by the guide wire 6 (in such a state that the balloon 2 is deflated).

When it is confirmed from the outside of the body by utilizing a contrast agent to be supplied from the connection part 31a to the balloon 2 that the balloon 2 reaches the left ventricle 11 and it is positioned in the vicinity of the pulmonary vein orifice 12a, for example, air is sent under pressure from the connection part 24a to expand the balloon 2. As a result, the balloon 2 is allowed to come into contact with and press the pulmonary vein orifice 12a to a strong extent, as shown in FIG. 2. It is to be noted herein that the shift valve 18 connected to the air vent tube 16 can be closed upon expansion of the balloon 2.

From the state of FIG. 2, for example, the balloon 2 and the catheter main body 1 can be filled with the heating liquid by supplying the balloon 2 with the heating liquid from the connection part 31a. Upon supplying the balloon 2 with the heating liquid, the air can be effectively withdrawn outward from the balloon 2 by the air vent tube 16 (by opening the shift valve 18), thereby allowing a smooth supply of the heating liquid to the balloon 2. It is to be noted herein that, if the air would be left inside the balloon 2 without being withdrawn completely, for example, the air in the balloon 2 is sucked from the connection part 24a toward the outside and the heating liquid is supplied again to the balloon 2. This operation can be repeated as needed.

Apart from the above procedures, a connection member comprising the elastic tube 40 and the extension tube 32 is prepared (to this connection member being connected the air vent valves 33 and 41). The connection member is filled with the heating liquid by using one of the air vent valves 33 and 41) and then the air vent valves 33 and 41 are closed.

The elastic tube 40 of the connection member filled with the heating liquid is set to the vibrator device RP. At this timing, the margin volume part 40A is set to have a length corresponding to the size of the balloon 2 by utilizing the indicators S1-S3, inclusive. The extension tube 32 is connected to the shift valve 31 before or after the setting of the margin volume part 40A. The air remaining in the path extending from the balloon 2 to the elastic tube 40 can be withdrawn from the air vent valve 33 or 41. Even in such a state that the elastic tube 40 is pressed down and closed with the roller 53, the air can also be withdrawn by the second air vent tube 41 from the top end portion of the elastic tube 40, i.e., the side of the margin volume part 40A.

Once it is confirmed that the path extending from the balloon 2 to the elastic tube 40 (i.e., the margin volume part 40A thereof), the high-frequency generating device 25 is operated to allow the heating electrode 3 to start heating. The operation status of the high-frequency generating device 25 can be subjected to feed-back control in order to permit the temperature within the balloon 2 to reach a predetermined temperature (60° C. for example), that is, the temperature to be detected with the thermocouple 4.

Upon heating with the heating electrode 3, the vibrator device RP is driven to rotatively drive the roller 54 in the predetermined direction of rotation. This permits a repetition of events comprising the application of pressure to the margin volume part 40A of the elastic tube 40 and the backward flow of the pressured heating liquid within the margin volume part 40A toward the catheter main body 1. The vibration of the heating liquid in the elastic tube 40 is transmitted to the heating liquid within the balloon 2 through the heating liquid of the catheter main body 1, thereby stirring the heating liquid in the balloon 2. This makes the temperature within the balloon 2 uniform as a whole due to the stirring of the heating liquid by vibration, although the heating liquid heated to a high temperature with the heating electrode 3 are likely to gather on top of the balloon 2. The pulmonary vein orifice 12a is cauterized by heating the balloon 2. As the balloon 2 is set to make the temperature uniform as a whole, the pulmonary vein orifice 12a can be cauterized to a uniform extent over the full length in the peripheral direction.

Although the present invention has been described by way of working examples, it is to be understood that the present invention is not limited to the working examples and various modifications and variations are possible as long as they are encompassed within the scope of the claims. For example, the heating electrode 3 may also be used as one of conductors for the thermocouple 4 and either one of the wires 14 and 15 can be removed (for example, Japanese Patent Application Publication No. 5-293,183 discloses an embodiment in which the wire of the heating electrode is also used as one of the wires for the thermocouple). It is further noted that the mode of cauterization is not limited to an annular cauterization of the pulmonary vein orifice and the present invention can also be applied to cauterization of a site of the heart or body tissues other than the heart.

The number or disposition of the rollers of the vibrator device RP may be two or more if there can be attained a state in which pressure is applied with the roller and a state in which no pressure is applied at all with the roller. For example, the roller 54 may comprise two rollers disposed at an interval of 180° in the direction of rotation of the rotary shaft 52, while the length of the guide surface G extends at an angle in the range of approximately 60° in the direction of rotation of the rotary shaft 52. In this embodiment, the margin volume part 40A is subjected to application of pressure and to backward flow at two times each as the rotary shaft 52 makes a full revolution. More specifically, the events consisting of the first application of pressure (the first application of pressure with the roller), the first backward flow, the second application of pressure (the second application of pressure) and the second backward flow occur in this order while the rotary shaft makes one full revolution. Moreover, the time required for the application of pressure and the time required for the backward flow are set each to be substantially equal to one another.

The number of the air vent valves may be one or three or more. For example, it may be disposed only at the edge or at the base end of the elastic tube 40. Further, the air vent valve may be disposed in another path connected to the elastic tube 40, e.g., at an intermediate portion of the extension tube. The elastic tube 40 can be connected to the connecter 20 or the catheter main body 2 without using the extension tube 32. It is not needed to separately fit the air vent tube 16 (in particular in order to reduce the outer diameter of the catheter main body 1). In this embodiment, the elastic tube 40 can be connected to the branch passage 22. The vibrator device RP can also be used for imparting vibration to a fluid, particularly liquid, even in the field other than the heating-type balloon catheter device. The predetermined positions (reference positions) to be aligned with the indicators S1 to S3, inclusive, set to the housing 51 may be set, for example, at the orifice edge surface of the inlet 51a or in the vicinity other than the orifice edge surface thereof. Moreover, the indicators may also be disposed at the base end portion of the elastic tube 40. In this embodiment, the predetermined position to be set to the housing 51 may be disposed at the orifice edge surface of the inlet 51a or in the vicinity thereof and the one that can be readily visible from the outside. It can be noted as a matter of course that the indicators S1-S3, inclusive, may be disposed at an intermediate portion in the longitudinal direction of the elastic tube 40. In this embodiment, the above predetermined position may be set in the vicinity of the guide surface G of the housing 51. Moreover, the indicator to be set to the elastic tube 40 may be only one while the housing 51 may be provided with plural predetermined positions (reference positions) to be aligned with the above one indicator at a spaced interval along the elastic tube 40 (along the guide surface G for example).

The function of one roller can be performed substantially by two rollers. For example, as shown in FIG. 4, in the event where the roller 54 is considered as a rear roller, a front roller is disposed as an auxiliary roller at a position immediately before this rear roller (the front roller itself rotates round the rotary shaft 52 (conducts an orbital motion) in substantially the same manner as the rear roller 54). It is provided, however, that, in the event where the front roller is at a position opposite to the guide surface G, the spaced distance from the guide surface G is set to become somewhat smaller than that from the rear roller 54. More specifically, the spaced distance from the guide surface G in the event where the front roller is disposed at a position opposite to the guide surface G can be set to a distance that can reduce the radial size of the elastic tube 40 yet cannot close to a full extent (a distance somewhat longer twice the length of the tube walls opposite to the elastic tube 40). This setting allows the front roller to reduce the size of the elastic tube 40, for example, by approximately a half to two-thirds and immediately thereafter the rear roller 54 to close the elastic tube 40 completely. As the size of the elastic tube 40 is reduced in advance by the front roller to a considerable extent in the manner as described above, even though it is not closed completely, this embodiment is preferred in terms of application of no crashing external force to the elastic tube 40, as compared with the embodiment in which the elastic tube 40 is closed to a full extent once by only one roller.

The object of the present invention is not limited to those as expressed above and encompasses those described impliedly as substantially preferred or as merits. Further, the present invention can be expressed also as a heating method.

What is claimed is:

1. An elastic tube device comprising an elastic tube which is expandable or constrictable in such a manner that tube walls of the elastic tube opposite to each other are caused to be closely attached to each other in a radial direction toward a direction in which the elastic tube is constrictable and that they are allowed to recover to their original shape due to their own elasticity when an external force is released;

wherein the elastic tube has a top end closed and a base end portion constituting a connection part for connecting to a catheter main body;

wherein said elastic tube has a margin volume part disposed on a top end side so as not to be pressed by the external force, and wherein a plurality of indicators are disposed on an outer peripheral surface of the elastic tube at a spaced interval in a longitudinal direction of the elastic tube, each of the plurality of indicators being indicative of a size of the margin volume part to be disposed in accordance with a size of a balloon in a heating-type balloon catheter device.

2. The elastic tube device as claimed in claim 1, wherein the plurality of indicators are formed from a top end portion side of the elastic tube to a base end portion side thereof.

3. The elastic tube device as claimed in claim 1, wherein an air vent valve for selectively opening the elastic tube to the atmosphere is connected to either one of the top end side and the base end portion of the elastic tube.

4. The elastic tube device as claimed in claim 1, wherein an air vent valve for selectively opening the elastic tube to the atmosphere is connected each to the top end side of the elastic tube and the base end portion thereof.

* * * * *